(12) United States Patent
Palasis

(10) Patent No.: US 6,506,408 B1
(45) Date of Patent: Jan. 14, 2003

(54) IMPLANTABLE OR INSERTABLE THERAPEUTIC AGENT DELIVERY DEVICE

(75) Inventor: Maria Palasis, Wellesley, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 1 day.

(21) Appl. No.: 09/615,764

(22) Filed: Jul. 13, 2000

(51) Int. Cl.[7] .............................. A61K 9/22; A61K 9/32
(52) U.S. Cl. .................... 424/468; 424/482; 435/320.1; 435/455; 514/44
(58) Field of Search ................................ 424/468, 482; 435/320.1, 455; 514/44

(56) References Cited

U.S. PATENT DOCUMENTS

| | | |
|---|---|---|
| 5,091,205 A | 2/1992 | Fan |
| 5,304,121 A | 4/1994 | Sahatjian |
| 5,554,147 A | 9/1996 | Batich et al. |
| 5,952,232 A * | 9/1999 | Rothman ................. 435/320.1 |

FOREIGN PATENT DOCUMENTS

| | | |
|---|---|---|
| EP | 0 963 761 A1 | 12/1999 |
| GB | 2 269 178 | 2/1994 |
| WO | WO96/39949 | 12/1996 |

* cited by examiner

Primary Examiner—Dave T. Nguyen
(74) Attorney, Agent, or Firm—Kenyon & Kenyon (57) ABSTRACT

Disclosed herein is an implantable or insertable therapeutic agent delivery device comprising a coating material provided on at least a portion of said device, said coating material prohibiting substantial release therefrom of a therapeutic agent at or below about a physiological pH and allowing substantial release therefrom of a therapeutic agent at or above about said physiological pH. Also disclosed herein are coating materials for the implantable or insertable therapeutic agent delivery device. The coating materials are preferably polymers derivatized to contain moieties that are cationically charged at a pH below their pKa values and which thus can attract negatively charged therapeutically agents at pH values below their pKa values and which become predominantly uncharged at pH values above about their pKa values and thus substantially release the negatively charged therapeutic agents at such pH values, which are preferably about physiological pH. Also disclosed are methods of derivatizing a polymer to contain such moieties and methods of providing a coating of the derivatized polymer onto at least a portion of a surface of an implantable or insertable therapeutic agent delivery device.

15 Claims, 2 Drawing Sheets

IMPLANTABLE OR INSERTABLE THERAPEUTIC AGENT DELIVERY DEVICE

FIELD OF THE INVENTION

The present invention relates to an apparatus and a method for localized delivery of therapeutic agents, and more particularly, to an implantable or insertable medical device having a coating, on at least a portion of a surface of the device, of a pH-sensitive polymer that allows release therefrom of a negatively charged therapeutic agent when contacted with a fluid at or above about a physiological pH.

BACKGROUND OF THE INVENTION

The systemic administration of drug agents, such as by transdermal or intravenous means, treats the body as a whole even though the disease to be treated may be localized. In such a case, systemic administration may not be desirable because the drug agents often have unwanted effects on parts of the body that are not intended to be treated, or because treatment of the diseased part of the body requires a high concentration of drug agent that may not be achievable by systemic administration. For example, when administered to a patient systemically, some drugs (e.g., chemotherapeutic drugs such as those used to treat cancer and other proliferative disorders) may cause undesirable side effects.

It is therefore often desirable to administer drug agents at a localized site within the body. Localized drug delivery is often desirable for the treatment of heart disease by delivery of a therapeutic agent to an occluded or stenosed vascular lumen as well as to deliver therapeutic agents to other target sites in the body including other occluded or stenosed body lumens.

Various methods have been proposed for such localized drug administration. For example, U.S. Pat. No. 5,304,121, which is incorporated herein by reference, discloses a method of delivering water-soluble drugs to tissue at a desired location of a body lumen wall. The method includes the steps of impregnating a hydrogel polymer provided as a coating on a balloon catheter or other implantable or insertable medical device with an aqueous drug solution, inserting the catheter into a blood vessel at a desired location, and expanding the balloon portion of the catheter against the surrounding tissue to allow the release of the drug from the hydrogel polymer coating. The drug is preferably released from the hydrogel polymer coating upon compression thereof against the body lumen wall. This method of drug delivery is convenient, but is limited by the fact that many drugs either release from the hydrogel before reaching the target site or are not released effectively when the target site is reached.

There remains a need for effective localized delivery of therapeutic agents. In particular, there exists a need for localized delivery of negatively charged therapeutic agents such as nucleic acid, for example. Nucleic acids are often difficult to remove when immobilized in a conventional polymer coating containing fixed positively charged moieties, i.e., moieties whose charge does not substantially depend on the ambient pH conditions. Thus, there is a need for a method for obtaining the release of therapeutic agents from a medical device at a target site within the body, particularly for the release of therapeutic agents from a medical device provided with a coating on at least a portion of a surface thereof which coating also contains therein or thereon a therapeutic agent, preferably a negatively charged therapeutic agent.

SUMMARY OF THE INVENTION

In one aspect, the present invention is directed to an implantable or insertable therapeutic agent delivery device comprising a coating material provided on at least a portion of a surface of the device, the coating material prohibiting substantial release therefrom of a therapeutic agent at or below about a physiological pH and allowing substantial release therefrom of a therapeutic agent at or above about physiological pH. In a preferred embodiment of the present invention, the coating material further comprises the therapeutic agent. Preferably, the therapeutic agent is negatively charged and the coating material comprises moieties that carry a positive charge at a pH at or below about physiological pH and are substantially uncharged at or above about physiological pH. Thus, the coating materials of the present invention are provided with moieties whose charge depends on pH, rather than being substantially fixed, i.e., substantially unaffected by varying pH conditions, such as occurs by known methods of derivatization of coating materials. Preferably, the moieties have a pKa less than about physiological pH. In a preferred embodiment, the polymeric material comprises a polymer which is preferably a poly(acrylic acid) polymer. In a particularly preferred embodiment, the poly(acrylic acid) polymer is a hydrogel polymer. In another preferred embodiment, moieties whose charge depends on pH as described herein are provided by compounds selected from the group consisting of aminoethyl pyridine or aminopropyl imidazole, each of which contains a moiety having a pKa less than about 7.4. In a preferred embodiment, the polymer is derivatized with at least one of these preferred compounds to result in a derivatized polymer containing moieties whose charge depends on pH as disclosed herein.

In another aspect, the present invention is directed to a method for delivering a therapeutic agent to a mammal by implanting or inserting into a mammal an implantable or insertable medical device according to the present invention.

In another aspect, the present invention is directed to a method of derivatizing a polymer by reacting, in the presence of 1-ethyl-3-(3-dimethylaminopropyl)-carbodiimide hydrochloride or dicyclohexylcarbodiimide, carboxyl groups in the polymer with a compound containing a moiety that has a positive charge at or below about physiological pH and that is substantially uncharged at or above about physiological pH. Preferably, the moiety in the compound reacted with the polymer has a pKa less than physiological pH of about than 7.4. The preferred compounds containing a moiety that has a pKa less than a physiological pH of about 7.4 are basic compounds of which aminoethyl pyridine and aminopropyl imidazole are most preferred.

In yet another aspect, the present invention is directed to a polymer made by the method described above.

In another aspect, the present invention is directed to a method of coating at least a portion of the surface of an implantable or insertable medical device comprising contacting the medical device with a coating material that prohibits substantial release therefrom of a therapeutic agent at or below about physiological pH and allows substantial release therefrom of a therapeutic agent at or above about physiological pH. In preferred embodiments, the medical device is contacted with the coating material by dipping the implantable or insertable medical device into a solution or suspension of the coating material, or by spraying a solution or suspension of the coating material onto at least a portion of the implantable or insertable medical device.

In yet another aspect, the present invention is directed to a method of coating at least a portion of an implantable or insertable medical device comprising contacting the medical device with a polymer and subsequently reacting, in the presence of 1-ethyl-3-(3-dimethylaminopropyl)-carbodiimide hydrochloride or dicyclohexylcarbodiimide, carboxyl groups in the polymer with a compound that contains a moiety that is positively charged at or below about physiological pH and that is substantially uncharged at or above about physiological pH, thereby forming a coating on at least a portion of the implantable or insertable medical device which prohibits substantial release therefrom of a therapeutic agent at or below about physiological pH and which allows substantial release therefrom of a therapeutic agent at or above about physiological pH.

BRIEF DESCRIPTION OF THE DRAWINGS

The various features of the invention will best be appreciated by simultaneous reference to the description that follows and the accompanying drawings, in which.

DEFINITIONS

An "implantable or insertable therapeutic agent delivery device" is any device which can be implanted and/or inserted into a mammalian body and which can also be adapted to provide localized delivery of a therapeutic agent. Such implantable or insertable therapeutic agent delivery devices that are within the scope of the present invention include, but are not limited to, stents of various types such as, for example, self-expandable and balloon-expandable vascular stents, stent grafts, biliary stents, colonic stents, bronchial/pulmonary stents, esophageal stents, and ureteral stents; catheters, including catheters having an expandable balloon portion, such as, for example, perfusion balloon catheters and needle injection catheters; filters such as blood clot filters; grafts such as vascular grafts and stent grafts; aneurysm filling coils and other coiled devices; transmyocardial revascularization ("TMR") devices; percutaneous myocardial revascularization ("PMR") devices, etc., as are known in the art; and devices such as hypodermic needles, soft tissue clips, holding devices, muscle implants such as spikes and plugs, as well as other types of medically useful needles. Such devices are generally constructed of biostable and biocompatible materials such as coated and non-coated metals, metal alloys, polymeric materials, ceramic materials and combinations of such materials. The devices are generally delivered to the target location within the body by known techniques. Delivery is optionally performed with a sheath covering the implantable or insertable medical device to protect premature release of the therapeutic agent provided on or within the coating material as described, prior to the device reaching the target location within the body. "Drug" and "therapeutic agent" are used interchangeably and refer to any substance used in the prevention, diagnosis, alleviation, mitigation, treatment or cure of any disease.

"Negatively charged therapeutic agent" refers to any drug or therapeutic agent that carries a negative charge.

"Physiological pH" refers to a normal pH of a physiological fluid in an animal, which is preferably a mammal such as a human. Physiological pH of a human is generally in the range of from about pH 7.2 to about 7.6.

"pKa" is defined as -log Ka; where Ka is the equilibrium constant for the dissociation of an acid to the hydronium ion ($H_3O^+$) and the counteranion of the acid.

DETAILED DESCRIPTION OF THE INVENTION

The coating material used in the present invention prohibits substantial release therefrom of a therapeutic agent at or below about a physiological pH and allows substantial release of the therapeutic agent at or above about physiological pH. Preferably, the coating material is a polymeric material, more preferably a hydrogel polymeric material. Even more preferably, the polymeric material is a polymer that has been derivatized with a compound that contains basic moieties that are positively charged at or below about physiological pH. The moieties are substantially uncharged at or above about physiological pH. Preferably, these moieties have a pKa that is less than a physiological pH of about 7.4. The preferred moieties are predominantly positively charged at a pH below their pKa value. Thus, the derivatized polymer is able to associate with a negatively charged therapeutic agent when contacted with the therapeutic agent at a pH below the pKa of the moieties, which is preferably less than about a physiological pH of 7.4. When the polymer containing such moieties is contacted with a physiological fluid such as blood having a pH greater than the pKa of the moieties, i.e., a pH preferably greater than about 7.4, the moieties begin to lose their positive charge. Thus, when contacted with a physiological fluid having a pH greater than the pKa of the moieties, the negatively charged therapeutic agent, such as nucleic acid, which is preferably associated with the moieties on the polymer through ionic binding, tends to be substantially released from the polymer coating. The negatively charged therapeutic agent tends to remain substantially unreleased from the derivatized polymer coating until contacted with a fluid or other substance, preferably a physiological fluid having a pH greater than the pKa of the moieties as described above. By "substantially released" or "substantially unreleased" is meant that at least about 50–60%, preferably about 70–80%, more preferably about 80–90%, and, most preferably, about 90–100% of the therapeutic agent is released or unreleased from its association with the coating material. Thus, at pH below physiological pH, the derivatized polymer coating contains positively charged moieties that attract and bind to the negatively charged therapeutic agent by ionic bonding. When the derivatized polymer of the invention is contacted with a physiological fluid or substance, such as blood or tissue, for example, which has a pH of about 7.4, the positively charged moieties lose their positive charge and no longer attract the negatively charged therapeutic agents. As a result, the negatively charged therapeutic agent is substantially released from the polymer at a desired location within the body. Since the positive charge on the moieties in the coating materials of the present invention is dependent on pH, the coating materials are able to effectively release therefrom a negatively charged therapeutic agent when the pH conditions to which the coating materials are exposed are such that the positively charged moieties become substantially uncharged.

One type of polymer that is useful in the present invention is an acrylic acid polymer. Such acrylic acid polymers that can be derivatized in accordance with the present invention are disclosed, e.g., in U.S. Pat. No. 5,091,205, which is incorporated herein in its entirety. However, it is to be understood that any acrylic acid polymer and, indeed, any of the poly(carboxylic acid) homopolymers and copolymers disclosed in U.S. Pat. No. 5,091,205 can be derivatized in the manner that is discussed in more detail below. Such acrylic acid polymers and other derivatizable polymers and sources thereof are well known to the ordinarily skilled artisan. Indeed, any polymeric or other material that contains moieties that are predominantly positively charged (i.e. about 50% or greater of the moieties are positively charged) at or below about their pKa values, which is preferably less than a physiological pH, and which are substantially uncharged at or above about a physiological pH, can be used to carry the negatively charged therapeutic agents in accordance with the present invention. Thus, any polymeric material which is biocompatible with the animal into which the implantable or insertable medical device is to be inserted and which bears moieties as described herein, or that can be derivatized to bear such moieties, can be used in accordance with the present invention. Examples of such derivatizable polymers include, but are not limited to, homopolymers of acrylic acid such as poly(acrylic acid), copolymers of acrylic acid such as copolymers of acrylic acid and acrylamide, poly(maleic acid), polysaccharides such as cellulosic ether polymers including carboxymethylcellulose, hyaluronic acid and other mucopolysaccharides found in mammalian fluids and connective tissues.

The coating material that is to be applied to at least a portion of the surface of an implantable or insertable medical device in accordance with the present invention can be made in the following manner. For purposes of example only, the starting polymer, that is derivatized in the manner described below, is an acrylic acid polymer. However, the polymer is not to be construed as being limited to acrylic acid polymers and may include, for example, other polymers as described above and that can be derivatized in a similar manner and function similarly. Polymeric coating materials that already contain the appropriate moieties that have a pKa less than about a physiological pH and which can thus associate with the negatively charged therapeutic agents in the manner described herein, e.g., poly(4-vinyl pyridine), polyethyleneimine and polypeptides including proteinaceous materials such as gelatin, collagen and albumin can also be applied to the surface of an implantable or insertable medical device to form the implantable or insertable therapeutic agent delivery devices of the present invention.

The coating material, which is preferably an acrylic acid polymer, can be derivatized and then applied to the surface of an implantable or insertable medical device. Alternatively, and in a preferred embodiment of the present invention, an underivatized polymer, such as an acrylic acid polymer or hydrogel polymer as described above can be initially applied to the surface of an implantable or insertable medical device and then derivatized in situ (i.e., while on the medical device) in a similar manner.

The implantable or insertable medical device of the present invention can be provided with the therapeutic agent associated with the coating. Alternatively, the medical device will have the derivatized coating applied thereto and the user of the medical device, prior to implantation or insertion thereof, can contact the coated medical device with the therapeutic agent so as to cause association of the therapeutic agent with the coating material prior to the insertion or implantation of the device. Thus, the implantable or insertable medical device of the present invention need not contain therein or thereon the negatively charged therapeutic agent, but may simply be coated with the derivatized polymer. In such a case, the therapeutic agent is applied to the coated device prior to use of the device.

Derivatization of an acrylic acid polymer will now be described in more detail. The carboxylic acid groups on a poly(acrylic acid) polymer, for example, are reacted with a compound containing both a basic moiety that functions to associate with the therapeutic agent in the pH dependent manner described herein and a substituent that binds to the carboxyl groups in the polymer. The substituent that binds to the carboxyl groups in the polymer may, for example, be an amino group in the compound containing the basic moiety. In such case, the compound containing the basic moiety will be bonded to the polymer through an amide linkage. The basic moiety in the compound will have a pKa value of less than about 7.4. The resultant derivatized polymer will thus contain basic moieties that are positively charged at a pH of less than their pKa values, which is preferably less than about a physiological pH, and thus have an affinity to associate with the negatively charged therapeutic agent. Association of the negatively charged therapeutic agent with the positively charged moieties of the derivatized polymer is preferably by ionic bonding. These basic moieties are substantially uncharged at or above a pH greater than their pKa values, and thus substantially release the negatively charged therapeutic agent associated therewith when the pH is increased beyond the pKa values.

Among preferred compounds containing a basic moiety that functions in the pH dependent manner described herein are aminoethyl pyridine and aminopropyl imidazole. The primary amino groups in aminoethyl pyridine and aminopropyl imidazole are able to bind through an amide linkage to, for example, carboxyl groups in a poly(acrylic acid) polymer to form a derivatized polymer, as described above, containing the pH dependent basic moieties. The basic moieties in aminoethyl pyridine and aminopropyl imidazole which function in the pH-dependent manner as described herein are, respectively, the pyridinyl and imidazolyl groups in these compounds. Pyridinyl and imadazolyl are merely exemplary preferred basic moieties that function in the pH dependent manner described herein. Thus, any compound containing a basic moiety having a pKa less than or equal to about physiological pH and which also has a substituent that can react with a derivatizable group in a polymer are useful in the present invention. Such basic moieties include, for example, cyclic and non-cyclic groups. The cyclic groups can be aromatic or non-aromatic and include heterocyclic and non-heterocyclic groups. Examples of non-aromatic heterocyclic groups include, but are not limited to, heterocyclic non-aromatic groups such as piperidinyl and pyrrolidinyl. Examples of aromatic heterocyclic groups include, but are not limited to, heterocyclic aromatic groups such as pyridinyl, imidazolyl, guaninyl, indolyl, pyrazolyl, pyridazinyl, pyrimidinyl, quinolinyl, pyrazinyl, thiazolyl , purinyl as well as the heterocyclic bases including guaninyl, adeninyl, cytosinyl, thyminyl and uracilyl. Examples of aromatic non-heterocyclic groups include, but are not limited to, pyridinyl, toluidinyl and anilinyl. Examples of non-cyclic groups include, but are not limited to guanidinyl and diamino(C1–C6)alkyl. It is to be understood that the substituent that bonds the compound containing the pH dependent basic moiety to a reactive group in the polymer is generally distinct from the basic moiety itself, which also forms part of the compound. Thus, the basic moiety in the compound attached to the polymer remains free to bind to the therapeutic agent. To further illustrate the present invention, the compound which is attached to the polymer may, for example, be a compound of the general formula H₂N—(CH₂)$_n$—(basic moiety).

In this exemplary compound, the primary amino group is able to attach the compound to the polymer by reacting with, for example, carboxyl moieties in the polymer, to form an amide linkage which links the compound containing the basic moiety to the polymer. The alkylene group, i.e. —(CH₂)$_n$—, in which n can range from 0 to 6, acts as a tether or spacer group which provides distance between the polymer and the basic moiety. Thus, the tether or spacer, which is optional, may be beneficial by providing a spacial separation between the polymer and the basic moiety in the compound attached to the polymer. This spacial separation may reduce steric hindrance between the therapeutic agent and the polymer to which the compound is attached, thus increasing the amount of the therapeutic agent which is effectively able to bind to the basic moiety in the pH dependent manner described herein. It is to be understood that the tether or spacer moiety is optional and, when present in the compound containing the basic moiety, is preferably a divalent organic radical that connects the basic moiety and the group in the compound, such as amino, that attaches to the reactive group in the polymer. Such divalent organic radicals include, but are not limited to, alkylene, alkyleneoxy, oxyalkylene, alkyleneamino, aminoalkylene, alkyleneoxyalkylene, alkylenethio, thioalkylene, alkylenecarbonyl, aminocarbonyl, carbonylamino, akyleneaminocarbonyl, aminocarbonylalkylene, oxy, oxycarbonyl, carbonyloxy, alkyleneoxycarbonyl, oxycarbonylalkylene, aminosulfonyl, or sulfonylamino. Of course, other divalent organic radicals can equally well serve as the spacer or tether group where such group is present in the compound containing the basic moiety.

Derivatization of a polymer by formation of an amide linkage between an compound containing the basic moiety and a carboxyl group containing polymer, such as poly (acrylic acid), may be conducted in the presence of a compound that facilitates reaction of an amino group in the compound containing the basic moiety with a carboxylic acid moiety in the polymer. Such facilitating compounds include, for example, 1-ethyl-3-(3-dimethylaminopropyl) carbodiimide hydrochloride, also known as EDC and dicyclohexylcarbodiimide, also known as DCC. EDC and DCC, for example, react with the carboxylic acid group in the polyacrylic acid, activating the carboxyl. The amino group in, for example, aminoethyl pyridine or aminopropyl imidazole, then couples to the activated carboxyl group forming an amide linkage. The resultant derivatized polymer then contains the desired basic moiety that functions in the pH dependent manner described herein. The reaction can be conducted in an aqueous or organic environment. Typically, EDC is used in an aqueous environment or in a mixed aqueous/organic environment. DCC is typically used in an organic environment. Where the reaction medium is organic or part organic, the organic component may be any conventionally used organic solvent including, but not limited to, DMF (dimethylformamide), methylene chloride, hexanes, methanol and mixtures thereof. In the derivatization with EDC, a soluble O-acyl isourea derivative is produced as a by-product, which is easily removed from the resultant derivatized polymer by washing, for example. It is to understood that EDC is merely exemplary of reagents that may facilitate connection of the compound containing the basic moiety to the polymer. Indeed, the ordinarily skilled artisan will readily appreciate numerous conventional reactions by which the compound containing the basic moiety can be attached, either directly or through the use of a facilitating compound such as EDC, to the derivatizable group in the polymer. Moreover, it is to be understood that the group in the compound containing the basic moiety that is attached to the derivatizable group in the polymer need not be an amino group, which is merely described herein for purposes of exemplification. Thus, it is entirely possible and within the scope of the present invention for the compound containing the basic moiety that functions in the pH dependent manner described herein to be linked to the polymer by other than an amide linkage, such as, for example, by an ester linkage, an ether linkage, etc.

As discussed above, amide linkages are preferred for connecting the compound containing the pH dependent basic moiety to the polymer. Such amide linkages will typically be formed by reaction of an amino group in the compound containing the basic moiety with a carboxyl group in the polymer. The preferred amino-group containing compounds which can be linked to the carboxyl groups using EDC as described above are those compounds containing, in addition to the basic moiety that functions in the pH dependent manner described herein, those compounds containing a primary amino group. As discussed above, particularly preferred amino-group containing compounds whose primary amino group can react with the carboxylic group in the above-described reaction to produce a derivatized hydrogel polymer that functions in accordance with the present invention include aminopropyl imidazole (pKa=6.92) and aminoethyl pyridine (pKa=5.19). These compounds are merely preferred amino-group containing compounds and the present invention is not to be construed as being limited thereto. Any amino-group containing compound that also has a basic moiety having a pKa less than about a physiological pH and which is substantially positively charged at below about a physiological pH and substantially uncharged at or above about a physiological pH may be employed to produce the derivatized polymers in accordance with the present invention. Indeed, the present invention is not limited to derivatization of a polymeric coating material by forming an amide linkage via an amino-group in the compound containing the pH dependent basic moiety as described herein. Any compound which contains a moiety that is substantially positively charged at or below about a physiological pH and which is substantially uncharged at or above about a physiological pH may be employed in the present invention, subject to its reactivity with a suitable functional group on a biocompatible material, preferably a biocompatible polymeric material as described herein.

The negatively charged therapeutic agent can be any therapeutic agent that will associate with the positively charged moieties on the derivatized polymer at below about a physiological pH, which is preferably about 7.4, and that will be substantially released therefrom at or above about a physiological pH. Such negatively charged therapeutic agents include, but are not limited to nucleic acids such as DNA, cDNA, RNA, antisense DNA or RNA, nucleotides, proteins such as aFGF and other acidic proteins, oligopeptides, cells, virus particles such as adenoviruses, adeno-associated viruses, alpha viruses and lentiviruses, liposomes or lipoplexes, polyplexes such as polylysine conjugates, "starburst" dendrimer conjugates, etc.; small and large molecular weight drugs including, but not limited to, heparin, hyaluronic acid, etc.

Polynucleotide sequences useful as therapeutic agents in the present invention include, for example, DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides useful in the invention can also code for therapeutic polypeptides. A polypeptide is understood to be any translation product of a polynucleotide regardless of size, and whether glycosylated or not. Therapeutic polypeptides include as a primary example, those polypeptides that can compensate for a defective or deficient species in an animal, or those that act through toxic effects to limit or remove harmful cells from the body. In addition, the polypeptides or proteins that can be incorporated into the coating material of the present invention, or whose DNA can be incorporated, include without limitation, angiogenic factors including acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor $\alpha$, hepatocyte growth factor and insulin like growth factor; growth factors; cell cycle inhibitors including CD inhibitors; thymidine kinase ("TK") and other agents useful for interfering with cell proliferation, including agents for treating malignancies. Still other useful factors, which can be provided as polypeptides or as DNA encoding these polypeptides, include the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

One or more negatively charged therapeutic agents may be associated with the coating material of the present invention. Moreover, it is also possible for the coating material to contain one or more other therapeutic agents that are not negatively charged. Thus, the coating material of the present invention, in addition to negatively charged therapeutic agents, can contain, for example, cationically charged, amphoteric or neutral therapeutic agents as well. Hence, each therapeutic agent in the coating material in accordance with the present invention need not be released from the coating material by the mechanism described herein in which the negatively charged therapeutic agents are released, i.e., preferably upon contact with fluid or tissue having a physiological pH. A preferred derivatized polymer in accordance with the present invention may thus contain one or more negatively charged therapeutic agents and one or more other therapeutic agents that are not necessarily ionically bound to the derivatized polymer coating as are the preferred negatively charged therapeutic agents.

Examples of other therapeutic agents (some of which may be negatively charged) that can be provided in or on a coating material in accordance with the present invention include, but are not limited to, anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, a polylysine-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

The therapeutic agents are in any form capable of associating with the polymer and subsequently being released from the polymer. Preferably, the therapeutic agent is applied to the polymer coating in solution in a suitable solvent, such as water, for example.

A polymer that has been derivatized in accordance with the method as described above can be applied in any conventional manner to the surface of the implantable or insertable medical device of the present invention. Such methods include, for example, dipping the implantable or insertable medical device into a solution or suspension of the derivatized polymer, followed by drying, or spraying the derivatized polymer onto the surface of the device. Any method for coating a surface with a polymeric material can be employed in this step.

An implantable or insertable medical device of the present invention is provided with a coating in accordance with the present invention that is sufficient to deliver a therapeutically effective amount of the therapeutic agent. The derivatized polymer is typically applied to at least a portion of the surface of an implantable or insertable medical device to a coating thickness of from about 1 $\mu$M to about 1000 $\mu$M, more preferably in the range of from about 10 $\mu$M to about 100 $\mu$M. However, it is to be understood that the appropriate thickness of the coating can vary outside of these preferred ranges and that the coating thickness that is most suitable may depend on the particular therapeutic agent contained therein or thereon. The amount of the therapeutic agent provided in or on the coating will be a therapeutically effective amount when released from the coating at the target location in the body. The amount of the therapeutic agent will typically range from 1 ng to 1 mg or more, and will, of course, depend on the specific therapeutic agent. Where the therapeutic agent is a protein, DNA, RNA, or other polynucleotide or nucleic acid, the therapeutically effective amount will typically range from about 1 $\mu$g to about 10 mg or more and, again, will depend on the specific DNA, RNA, or other polynucleotide protein or nucleic acid. Where the therapeutic agent is a virus, the therapeutically effective amount will again vary depending on the specific virus, but will typically range from about $1 \times 10^7$ to about $1 \times 10^{13}$ infectious units, more preferably from about $1 \times 10^9$ to about $1 \times 10^{11}$ infectious units.

Alternatively, and in a preferred embodiment of the present invention, an underivatized polymer, which may be in crosslinked or un-crosslinked form is applied to at least a portion of the surface of the implantable or insertable medical device directly by any of the coating methods known in the art. Once the underivatized polymer is applied, the derivatization reaction as described above is utilized to bind the compound containing the basic moiety to the carboxylic acid groups in the poly(acrylic acid).

The device of the present invention can also be formed by applying a commercially available polymer that contains moieties having a pKa less than about a physiological pH and which are thus substantially positively charged at a pH below about a physiological pH and are substantially uncharged at a pH at or above about a physiological pH. Such a coating functions in the manner described above with respect to release of the negatively charged therapeutic agent at or above about a physiological pH. Such polymers include, for example, poly(4-vinyl pyridine), polyethyleneimine, polypeptides including proteinaceous materials such as gelatin, collagen and albumin.

The therapeutic agent can be associated with the positively charged moieties in the coating material by contacting, e.g., the coated medical device of the present invention with a solution or suspension of the negatively charged therapeutic agent for a period of time sufficient to allow a therapeutically effective amount of the negatively charged therapeutic agent to become associated with the positively charged moieties.

In another embodiment of the invention, multiple coating layers are provided on the implantable or insertable medical device in accordance with the methods of the present invention. While each layer need not function similarly to the coating material of the present invention, at least one layer on the implantable or insertable medical device will function in accordance with the present invention. Thus, it may be desired to provide a coating of a derivatized polymer in accordance with the present invention onto an implantable or insertable medical device to which has previously been applied one or more layers of other coating materials. Multiple coating layers may be desirable to produce a coating thickness required for a specific dose or loading of therapeutic or bioactive agents or to provide coating layers suitable for particular therapeutic agents or combinations of therapeutic agents or to provide differential release rates of therapeutic agents.

It is to be understood that the mechanism of release of the therapeutic agent need not be the same for each of any multiple layers. Hence, any layer may have therapeutic agents incorporated therein or thereon in a manner different from the association of the negatively charged therapeutic agents in accordance with the present invention. Different drugs or different concentrations of drugs can be incorporated in or on any of the multiple layers, and the mechanism of release of such drugs from those layers may differ from the release of the drugs from any layer containing a derivatized polymer in accordance with the present invention.

Coating formulations used to coat at least a portion of the surface of an implantable or insertable medical device generally contain the formulation components dissolved or suspended in a solvent medium. A coating formulation typically includes, for example, the following components: one or more polymers or copolymers, which form the matrix of the dried coating; one or more drugs or therapeutic agents, biostatic agents, anti-microbial agents or other bioactive agents; and a selection of one or more solvents which are typically removed during drying, e.g., by evaporation.

A solvent medium for a subsequently applied coating layer can partially dissolve or otherwise disrupt the coating material of any previously applied layers, or can even cause leaching or removal of a therapeutic agent from a previously applied coating layer. Thus, when it is desired to apply multiple coating layers to an implantable or insertable medical device, it is preferred to use a combination of solvents, which includes at least one poor solvent for the coating formulation components such that the solubility of the lower (i.e. previously applied) layers is limited. The appropriate selection of solvents minimizes, during application of additional layers, any deleterious affect on previously applied layers.

The polymers used in forming multiple coating layers can be any polymers which are conventionally used as coating materials for implantable or insertable medical devices. The solvents are selected such that multiple layers can be applied without removing or affecting the properties of the previous layers. In order to achieve this, a solvent/non-solvent combination is preferably used such that at least one of the selected solvents is considered a good solvent for the polymer and active components, and at least one solvent is selected that is a poor solvent for the polymer and active components. Additionally, a multi-layer coating may be applied where the solvent or combination of solvents used for each layer is the same or different. The type of solvent or solvent ratio may be progressively changed to include a greater amount of one of the solvents as the layers are built up. The solvents are preferably selected to minimize or prevent solubilization of the lower layers during the application of subsequent layers. An additional reason this may be done is to increase interfacial mixing and possibly enhance other properties of the multi-layered coating, such as interfacial adhesion between layers.

Furthermore, the coatings may be applied using a variety of techniques, such as dip coating, spraying, and spin coating, or any other method commonly known to the ordinarily skilled artisan.

The invention will now be described in greater detail in the following examples which are provided to illustrate preferred embodiments of the present invention and are therefore not meant to be construed as limiting the scope of the present invention.

EXAMPLES 1–6

Derivatization of a Hydrogel Polymer Coating on a Balloon Catheter with Aminopropylimidazole

Example 1

An angioplasty balloon catheter was provided with a coating of HYDROPLUS poly(acrylic acid) polymer as disclosed in U.S. Pat. No. 5,091,205, which is incorporated herein in its entirety.

The balloon catheter coated with the HYDROPLUS coating was placed into 200 $\mu$L of a solution of (2-[N-morpholino]ethane sulfonic acid), "MES," to swell the HYDROPLUS coating. 2 $\mu$L of aminopropylimidazole and 500 $\mu$L of MES buffer were added. 10 mg of 1-ethyl-3-(3-dimethylaminopropyl)carbodiimide hydrochloride, "EDC," (from Pierce, Rockford Ill.) were dissolved in 1 mL of deionized ultrafiltered water and 100 $\mu$L of this solution were then added to the solution containing the HYDROPLUS coated balloon catheter and the aminopropylimidazole. The derivatized HYDROPLUS coating on the balloon catheter was then washed with PBS (phosphate-buffered saline).

The balloon catheter provided with the derivatized HYDROPLUS coating was then contacted with 0.1 M hydrochloric acid to maximize the concentration of positively charged moieties in the derivatized HYDROPLUS coating. The balloon catheter was then dipped into a solution of methyl orange, a negatively charged dye. It was observed that the HYDROPLUS coating was red upon removal of the catheter containing the derivatized HYDROPLUS coating from the methyl orange solution. A control catheter provided with an underivatized HYDROPLUS coating was also dipped into the methyl orange solution and was red upon removal therefrom. When the control catheter and the catheter containing the derivatized coating were contacted with water, the control catheter was clear, indicating that the methyl orange was completely released from the underivatized HYDROPLUS coating, whereas the catheter containing the derivatized coating was orange, indicating only a partial release of the methyl orange from the derivatized coating. A catheter containing a derivatized HYDROPLUS coating which was red from contact with methyl orange solution was also dipped into PBS at a pH of 7.4. Upon removal from the PBS, the catheter was clear, indicating that the methyl orange was completely removed therefrom upon contact with PBS at a pH of 7.4.

Example 2

The procedure of Example 1 was repeated except that 4 μL of aminopropylimidazole were used. The balloon catheter showed staining upon contact with methyl orange.

Example 3

The procedure of Example 1 was repeated except that 8 μL of aminopropylimidazole were used. The balloon catheter showed no staining upon contact with methyl orange.

Example 4

The procedure of Example 1 was repeated except that 150 μL of EDC were used. The balloon catheter showed staining upon contact with methyl orange.

Example 5

The procedure of Example 4 was repeated except that 4 μL of aminopropylimidazole were used. The balloon catheter showed staining upon contact with methyl orange.

Example 6

The procedure of example 4 was repeated except that 8 μL of aminopropylimidazole were used. The balloon catheter showed no staining upon contact with methyl orange.

Examples 7–12

Derivatization of a Hydrogel Polymer Coating on a Balloon Catheter with Aminoethylpyridine Each of Examples 7–12 were performed according to the procedure of Example 1, except that aminoethylpyridine was used in place of aminopropylimidazole.

Example 7

The procedure of Example 1 was repeated except that aminoethylpyridine was used in place of aminopropylimidazole. The balloon catheter showed staining upon contact with methyl orange.

Example 8

The procedure of Example 7 was repeated except that 4 μL of aminoethylpyridine were used. The balloon catheter showed staining upon contact with methyl orange.

Example 9

The procedure of Example 7 was repeated except that 8 μL of aminoethylpyridine were used. The balloon catheter showed no staining upon contact with methyl orange.

Example 10

The procedure of Example 7 was repeated except that 150 μL of EDC were used. The balloon catheter showed staining upon contact with methyl orange.

Example 11

The procedure of Example 1 was repeated except that 4 μL of aminoethylpyridine were used. The balloon catheter showed staining upon contact with methyl orange.

Example 12

The procedure of example 1 was repeated except that 8 μL of aminoethylpyridine were used. The balloon catheter showed no staining upon contact with methyl orange.

Figure 1:
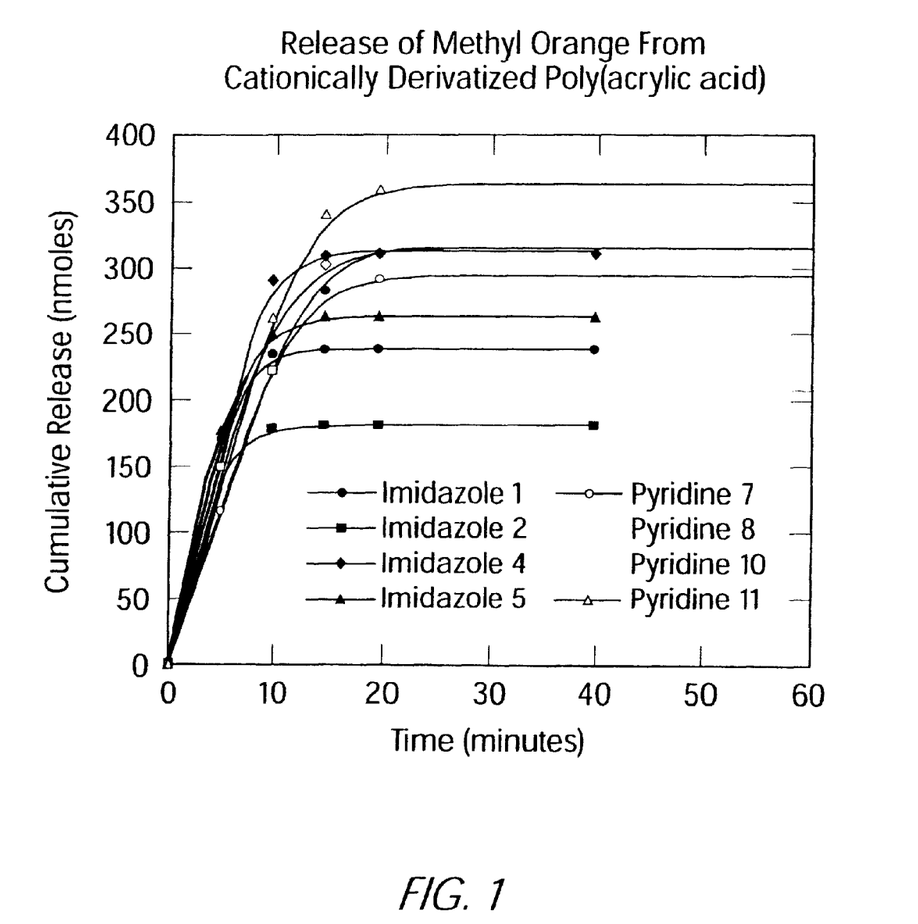
FIG. 1 shows the release in phosphate-buffered saline (PBS), pH 7.4, of methyl orange from balloon catheters provided with a coating of a hydrogel acrylic acid polymer derivatized with aminopropyl imidazole or aminoethyl pyridine in accordance with preferred embodiments of the present invention.

These release of methyl orange from the cationically derivatized HYDROPLUS coatings the balloon catheters prepared according to Examples 1, 2, 4, 5, 7, 8, 10, and 11 in PBS buffer at pH 7.4 are shown in FIG. 1. Since the balloon catheters prepared according to Examples 3, 6, 9 and 12 did not show staining with methyl orange, there is no release data in FIG. 1 for these balloon catheters.

The results of Examples 1–12 are present for clarity in the following Table:

| Example | Amine | EDC | Staining with methyl orange |
|---|---|---|---|
| 1 | 2 μL aminopropylimidazole | 100 μL | stained |
| 2 | 4 μL aminopropylimidazole | 100 μL | stained |
| 3 | 8 μL aminopropylimidazole | 100 μL | not stained |
| 4 | 2 μL aminopropylimidazole | 150 μL | stained |
| 5 | 4 μL aminopropylimidazole | 150 μL | stained |
| 6 | 8 μL aminopropylimidazole | 150 μL | not stained |
| 7 | 2 μL aminoethylpyridine | 100 μL | stained |
| 8 | 4 μL aminoethylpyridine | 100 μL | stained |
| 9 | 8 μL aminoethylpyridine | 100 μL | not stained |
| 10 | 2 μL aminoethylpyridine | 150 μL | stained |
| 11 | 4 μL aminoethylpyridine | 150 μL | stained |
| 12 | 8 μL aminoethylpyridine | 150 μL | not stained |

Example 13–14

Release of Plasmid DNA from Balloon Catheter having Derivatized Hydrogel Polymer Coating

Example 13

A balloon catheter containing a HYDROPLUS coating derivatized with aminopropylimidazole was prepared in the manner of Example 4. A solution of plasmid DNA (approximately 5,000 bases) having a concentration of 167

μg/mL was used 50 μL of this DNA solution was diluted with 450 μL of PBS at a pH of 5.7. 200 μL of this solution were then added to an Eppendorf tube into which solution the balloon catheter containing the derivatized HYDROPLUS coating was dipped for approximately 20 minutes.

Example 14

The method of Example 13 was repeated, except that a balloon catheter containing a HYDROPLUS coating derivatized with aminoethylpyridine prepared in the manner of Example 11 was used.

Figure 2:
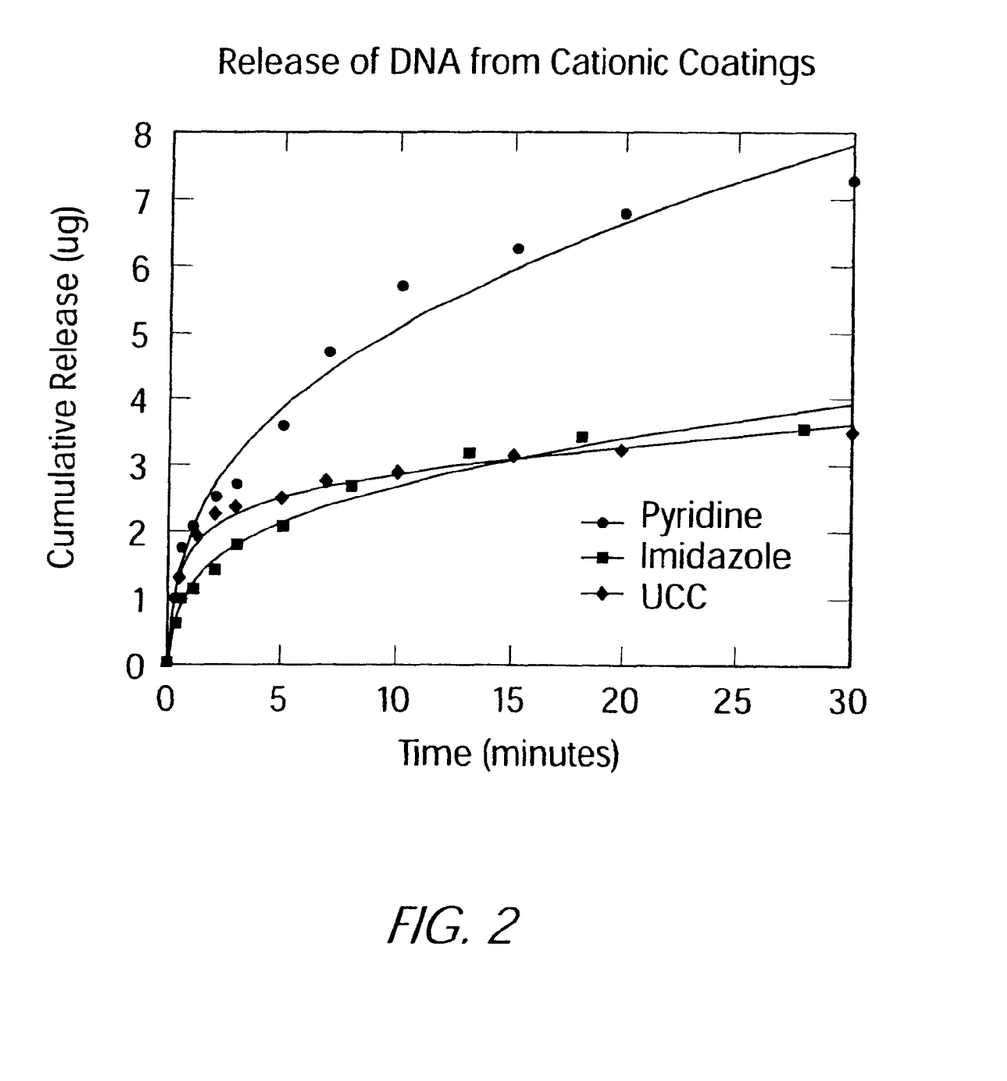
FIG. 2 shows the release in PBS, pH 7.4, of plasmid DNA from balloon catheters provided with a coating of a hydrogel acrylic acid polymer derivatized with aminopropyl imidazole or aminoethyl pyridine in accordance with preferred embodiments of the present invention.

The release, in PBS buffer at pH 7.4, of DNA from the catheters used in Examples 13 and 14 are compared in FIG. 2 with the release of DNA from a catheter containing an underivatized HYDROPLUS coating obtained from Union Carbide Corporation, which contained quaternary ammonium groups (having fixed positive charge).

Example 15

A balloon-expandable angioplasty catheter is coated with HYDROPLUS poly(acrylic acid) hydrogel polymer by dipping the balloon portion of the catheter for approximately 1 minute into a 1% solution of the polymer in dimethylformamide (DMF) solvent. The catheter is removed from the solution and dried at 60° C. for about 30 minutes. In this manner, a hydrogel polymer coating of approximately 2–20 μm is formed on the expandable balloon portion of the catheter. The coating is then derivatized with aminopropyl imidazole in the manner described in Example 4. The catheter, having the derivatized coating thereon, is then dipped for approximately 20 minutes into an aqueous $1 \times 10^{12}$ viral particles/ml dispersion of a negatively charged adenovirus vector, the dispersion having a pH of approximately 6.8. The catheter is removed from the dispersion of the negatively charged adenovirus. The catheter, via a conventional percutaneous transdermal angioplasty procedure, is then surgically inserted into a human subject and positioned adjacent the walls of a partially occluded coronary artery in the subject. The balloon portion is then expanded against the walls of the occluded coronary artery and allowed to remain in the expanded state for approximately 2 minutes. Upon contact of the derivatized hydrogel coating provided on the balloon with the wall tissue of the partially occluded artery (pH approximately 7.4), the negatively charged adenovirus is substantially released from the hydrogel coating and is taken up by the wall tissue of the occluded artery.

I claim:

1. An implantable or insertable therapeutic agent delivery device comprising a coating material provided on at least a portion of said device, said coating material prohibiting substantial release therefrom of a therapeutic agent at or below about a physiological pH and allowing substantial release therefrom of a therapeutic agent at or above about said physiological pH, wherein said therapeutic agent is negatively charged and said coating material comprises a biocompatible polymer comprising basic moieties that have a pKa value of less than about 7.4.

2. The device of claim 1 wherein said coating material further comprises said therapeutic agent.

3. The device of claim 2 wherein said moieties carry a positive charge at a pH at or below about said physiological pH and are substantially uncharged at or above about said physiological pH.

4. The device of claim 1 wherein said physiological pH is in the range from about 7.2 to about 7.6.

5. The device of claim 4 wherein said physiological pH is about the pH of mammalian blood.

6. The device of claim 5 wherein said pH is about 7.4.

7. The device of claim 1 wherein said biocompatible polymer comprises a hydrogel polymer.

8. The device of claim 7 wherein said hydrogel polymer comprises a poly(acrylic acid) polymer.

9. The device of claim 8 wherein said moieties are provided by at least one compound selected from the group consisting of aminoethyl pyridine and aminopropyl imidazole.

10. The device of claim 1 which is a stent or balloon catheter.

11. A method of delivering a therapeutic agent to a mammal comprising implanting or inserting the device of claim 1 into a mammal.

12. The device of claim 1 wherein said negatively charged therapeutic agent is selected from the group consisting of DNA, RNA, polynucleotides, oligopeptides, viruses, drugs and nonviral vectors comprising a therapeutic nucleic acid.

13. A method of coating at least a portion of an implantable or insertable medical device comprising contacting said medical device with a coating material that prohibits substantial release therefrom of a therapeutic agent at or below about a physiological pH and allows substantial release therefrom of a therapeutic agent at or above said physiological pH, wherein said therapeutic agent is negatively charged and said coating material comprises a biocompatible polymer comprising basic moieties that have a pKa value of less than about 7.4.

14. The method of claim 13 wherein said medical device is contacted with said coating material by a method selected from the group consisting of dipping said device into or spraying onto said device a solution or suspension of said coating material.

15. A method of coating at least a portion of an implantable or insertable medical device comprising contacting said medical device with a polymer and subsequently reacting, in the presence of 1-ethyl-3-(3-dimethylaminopropyl)-carbodiimide hydrochloride, carboxyl groups in said polymer with a compound containing a moiety that carries a positive charge at or below about a physiological pH and that is substantially uncharged at or above said physiological pH, thereby forming a coating on at least a portion of the implantable or insertable medical device which prohibits substantial release therefrom of a therapeutic agent at or below about a physiological pH and which allows substantial release therefrom of a therapeutic agent at or above about said physiological pH, wherein said therapeutic agent is negatively charged and said coating material comprises a biocompatible polymer comprising basic moieties that have a pKa value of less than about 7.4.

* * * * *